United States Patent
Goldkorn et al.

(10) Patent No.: US 10,261,088 B2
(45) Date of Patent: Apr. 16, 2019

(54) METHOD FOR CANCER DETECTION, DIAGNOSIS AND PROGNOSIS

(71) Applicants: California Institute of Technology, Pasadena, CA (US); University of Southern California, Los Angeles, CA (US)

(72) Inventors: Amir Goldkorn, Beverly Hills, CA (US); Yu-Chong Tai, Pasadena, CA (US); Tong Xu, Pasadena, CA (US); Bo Lu, Pasadena, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 320 days.

(21) Appl. No.: 14/877,711

(22) Filed: Oct. 7, 2015

(65) Prior Publication Data

US 2016/0252514 A1 Sep. 1, 2016

Related U.S. Application Data

(63) Continuation of application No. 14/020,313, filed on Sep. 6, 2013, now Pat. No. 9,182,387, which is a
(Continued)

(51) Int. Cl.
| | |
|---|---|
| *G01N 33/574* | (2006.01) |
| *C12N 5/09* | (2010.01) |
| *C12Q 1/6806* | (2018.01) |
| *C12Q 1/6886* | (2018.01) |
| *G01N 33/50* | (2006.01) |

(Continued)

(52) U.S. Cl.
CPC ..... *G01N 33/57496* (2013.01); *C12N 5/0693* (2013.01); *C12Q 1/6806* (2013.01);
(Continued)

(58) Field of Classification Search
CPC .. G01N 33/57496; G01N 1/30; G01N 1/4077; G01N 33/5094; G01N 2333/9128;
(Continued)

(56) References Cited

U.S. PATENT DOCUMENTS

| 5,856,096 A | 1/1999 | Windle et al. |
| 6,598,750 B2 * | 7/2003 | Tai ..................... B01D 39/2093 |
| | | 210/490 |

(Continued)

FOREIGN PATENT DOCUMENTS

| WO | 2006/100366 A2 | 9/2006 |
| WO | 2010/135603 A2 | 11/2010 |

OTHER PUBLICATIONS

Zheng et al., Membrane microfilter device for selective capture, electrolysis and genomic analysis of human circulating tumor cells, Journal of Chromatography, May 2007 (Year: 2007).*
(Continued)

*Primary Examiner* — Sally A Merkling
(74) *Attorney, Agent, or Firm* — Kilpatrick Townsend & Stockton LLP

(57) ABSTRACT

The present invention provides a method for diagnosing cancer, predicting a disease outcome or response to therapy in a patient sample. The method involves isolating a circulating tumor cell (CTC), for example, a viable CTC, from a sample using a parylene microfilter device comprising a membrane filter having or consisting of a parylene substrate, which has an array of holes with a predetermined shape and size; and detecting and quantifying telomerase activity in blood circulating tumor cells. The invention further provides methods of using cells live-captured in various applications.

15 Claims, 10 Drawing Sheets

Specification includes a Sequence Listing.

Related U.S. Application Data continuation of application No. 12/784,446, filed on May 20, 2010, now Pat. No. 8,551,425.

(60) Provisional application No. 61/180,021, filed on May 20, 2009.

(51) Int. Cl.
*G01N 1/30* (2006.01)
*G01N 1/40* (2006.01)

(52) U.S. Cl.
CPC ............ *C12Q 1/6886* (2013.01); *G01N 1/30* (2013.01); *G01N 1/4077* (2013.01); *G01N 33/5094* (2013.01); *C12N 2503/00* (2013.01); *C12Q 2600/118* (2013.01); *C12Y 207/07049* (2013.01); *G01N 2001/4088* (2013.01); *G01N 2333/9128* (2013.01); *Y10T 436/25375* (2015.01)

(58) Field of Classification Search
CPC .......... G01N 2001/4088; C12N 5/0693; C12N 2503/00; C12Q 1/6886; C12Q 1/6806; C12Q 2600/118; C12Y 207/07049; Y10T 436/25375
See application file for complete search history.

(56) References Cited

U.S. PATENT DOCUMENTS

| | | | |
|---|---|---|---|
| 7,166,443 B2 * | 1/2007 | Walker | A61M 1/36 435/286.5 |
| 8,551,425 B2 | 10/2013 | Goldkorn et al. | |
| 2004/0142463 A1 | 7/2004 | Walker et al. | |
| 2006/0254972 A1 | 11/2006 | Tai et al. | |
| 2007/0025883 A1 | 2/2007 | Tai et al. | |
| 2008/0057505 A1 | 3/2008 | Lin et al. | |
| 2009/0188864 A1 | 7/2009 | Zheng et al. | |
| 2011/0053152 A1 | 3/2011 | Goldkorn et al. | |
| 2012/0129252 A1 * | 5/2012 | Seubert | B01D 63/087 435/325 |
| 2012/0141337 A1 | 6/2012 | Maltezos et al. | |
| 2014/0038271 A1 | 2/2014 | Goldkorn et al. | |

OTHER PUBLICATIONS

U.S. Appl. No. 12/784,446 , "Notice of Allowance", dated Jun. 11, 2013, 6 Pages.

U.S. Appl. No. 12/784,446 , "Office Action", dated Apr. 16, 2012, 7 Pages.

U.S. Appl. No. 12/784,446 , "Office Action", dated Sep. 13, 2012, 8 Pages.

U.S. Appl. No. 14/020,313 , "Non Final Office Action", dated Aug. 4, 2014, 9 pages.

U.S. Appl. No. 14/020,313 , "Non-Final Office Action", dated Dec. 23, 2014, 11 pages.

U.S. Appl. No. 14/020,313 , "Notice of Allowance", dated Jul. 7, 2015, 7 pages.

PCT/US2010/035684, "International Search Report and Written Opinion" dated Apr. 4, 201, 10 Pages.

Xu, et al., "A Cancer Detection Platform Which Measures Telomerase Activity from Live Circulating Tumor Cells Captured on a Microfilter", *Cancer Res.*, vol. 70 (16), pp. 6420-6426 (2010).

* cited by examiner

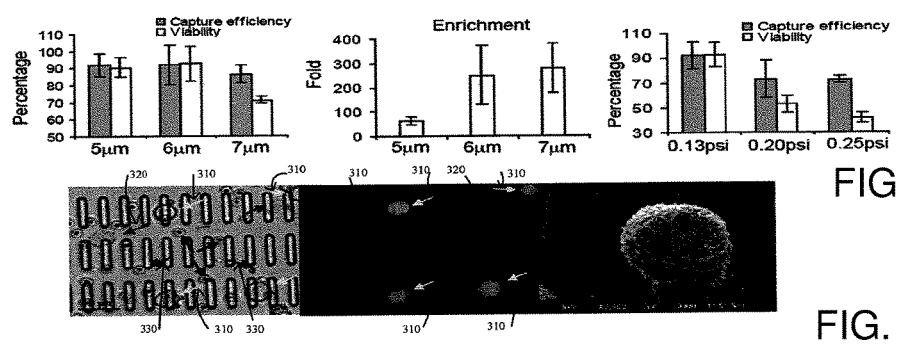
FIG. 3A
FIG. 3B
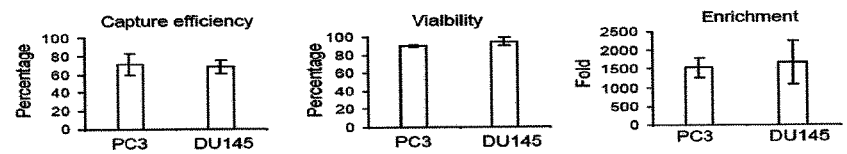
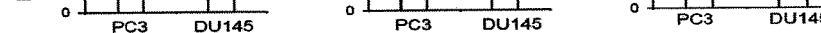
FIG. 3C
On-filter culture
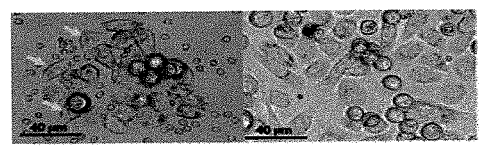
Off-filter culture
Day 3     Day 6
FIG. 3D FIG. 8A 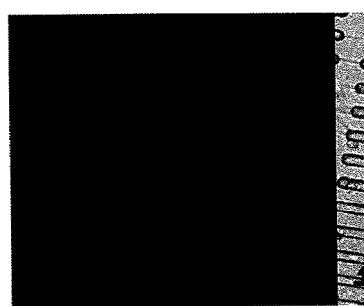 FIG. 8B 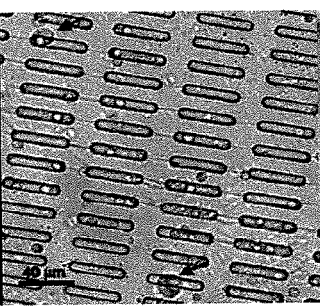 FIG. 8C 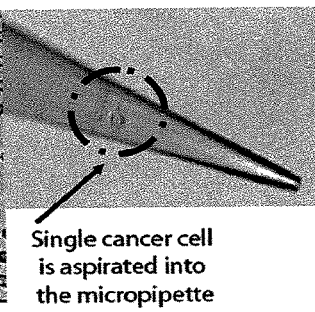
Single cancer cell is aspirated into the micropipette
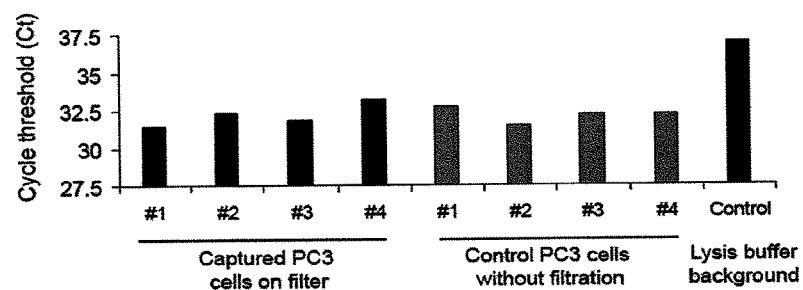
FIG. 8D

METHOD FOR CANCER DETECTION, DIAGNOSIS AND PROGNOSIS

CROSS-REFERENCES TO RELATED APPLICATIONS

This application claims priority to U.S. Provisional Patent Application No. 61/180,021, filed May 20, 2009, which is herein incorporated by reference in its entirety for all purpose.

BACKGROUND OF THE INVENTION

Cancer is a major health concern worldwide, accounting for millions of deaths and untold pain and suffering each year. The biologic heterogeneity of this disease and the vast populations afflicted pose the pivotal questions of whom to treat and with which therapies, challenges that can only be addressed through the development of more accurate and informative biomarkers. Peripheral blood circulating tumor cells (CTCs) recently have been detected and shown to have prognostic and predictive value in breast and prostate cancer (see, Ignatiadis, M., et al., *J Clin Oncol* 2007; 25:5194-202; Pachmann, K., et al., *J Clin Oncol* 2008 (ASCO Annual Meeting abstr 11001); Rack, B. K., et al., *J Clin Oncol* 2008 (ASCO Annual Meeting abstr 503); Goodman, O. B., et al., *J Clin Oncol* 2008 (ASCO Annual Meeting abstr 5169); Attard, G., et al., *J Clin Oncol* 2008 (ASCO Annual Meeting abstr 5072); Fizazi, K., et al., *Ann Oncol* 2007; 183:518-21; and Shaffer, D. R., et al., *Clin Cancer Res* 2007; 13:2023-9). However, these preliminary efforts have been hampered by two significant limitations: (1) CTC isolation and (2) CTC detection. Collecting CTCs has involved a laborious process that employs multiple antibody binding and magnetic bead sorting steps, requiring expensive reagents and equipment, and ultimately yielding a relatively small population of CTCs, which may vary from sample to sample depending on the expression pattern of cell surface markers used in this method. Currently, CTCs are isolated from blood by methods which rely on immuno-magnetic binding of cell surface epithelial cell adhesion molecules (EpCAMs), an expensive, labor-intense approach that is limited to EpCAMexpressing tumors (see, Cristofanilli, M., et al., *N Engl J Med* 2004; 351:781-91; and Nagrath. S., et al., *Nature* 2007; 450:1235-9). An alternative platform using a novel parylene-C pore microfilter which traps CTCs quickly and efficiently based on their size differential from other blood cells (See, Zheng, S., et al., *J Chromatogr A* 2007; 1162:154-61). However, like the EpCAMbased approach, the pore microfilter still relied on fixation, staining, and visual enumeration of captured cells, a laborious and subjective process prone to reader/operator variability. Nevertheless, regardless of the isolation method, it is difficult to derive accurate diagnostic, prognostic or predictive data from absolute numbers of CTCs because of the relative paucity of these cells in peripheral blood.

Therefore, there is a need to develop simple yet highly sensitive and specific cancer detection systems and methods to overcome the above and other problems. The detection systems and methods can be used as a diagnostic, prognostic or predictive assay in patients.

BRIEF SUMMARY OF THE INVENTION

The present invention relates to novel systems and methods for cancer detection, analysis and characterization. More specifically, the invention is directed to a method for diagnosing a cancer or predicting a disease outcome in a patient sample. The method includes the use of a constant low-pressure system coupled to a parylene filtration device to rapidly and efficiently capture circulating tumor cells (CTC) and detect and quantify telomerase activity in blood CTCs. The method is useful as a diagnostic, prognostic and predictive technique in cancer. For example, the system and method are capable of cell capture from 1 ml of whole blood in less than 5 minutes, achieving greater than 90% capture efficiency, greater than 90% cell viability and greater than 200-fold sample enrichment.

In one aspect, the present invention provides a method for diagnosing cancer or predicting a disease outcome in a patient sample. The method includes, for example, isolating a circulating tumor cell from a sample using a parylene microfilter device comprising a membrane filter having or consisting of a parylene substrate, which has an array of holes with a predetermined shape and size; and determining the telomerase activity of the isolated circulating tumor cell using, for example, a telomerase activity assay.

In another aspect, the present invention provides a method for detecting and quantifying the telomerase activity of a circulating tumor cell. The method includes, for example, isolating the circulating tumor cell from a sample using a parylene microfilter device comprising a membrane filter having or consisting of a parylene substrate, which has an array of holes with a predetermined shape and size; and determining the telomerase activity of the isolated circulating tumor cell using a quantitative PCR telomerase activity assay.

In still another aspect, the present invention provides a method for enrichment of circulating tumor cells. The method includes passing a sample containing a circulating tumor cell through a parylene microfilter device comprising a membrane filter having or consisting of a parylene substrate, which has an array of holes with a predetermined shape and dimension; and capturing said circulating tumor cell on the membrane filter, wherein the enrichment of circulating tumor cells is greater than at least 200-1500 fold.

In a further aspect, the invention provides a system for isolating a circulating tumor cell. The system includes a parylene microfilter device comprising a membrane filter having or consisting of a parylene substrate having an array of holes with a predetermined shape and dimension; and a constant pressure delivery system coupled to the parylene microfilter device for maintaining a constant pressure.

In another aspect, the present invention provides a method for measuring mRNA expression levels of a gene in a circulating tumor cell (CTC). The method includes isolating a CTC from a sample using a parylene microfilter device comprising a membrane filter having or consisting of a parylene substrate, which has an array of holes with a predetermined shape and size; and measuring the mRNA expression levels of the gene in the CTC.

In yet another aspect, the present invention provides a method for staining a circulating tumor cell (CTC). The method includes isolating a CTC from a sample using a parylene microfilter device comprising a membrane filter having or consisting of a parylene substrate, which has an array of holes with a predetermined shape and size; and staining the CTC with a dye or an antibody conjugated to a dye.

In yet another aspect, the present invention provides a method for propagating a circulating tumor cell (CTC) in culture. The method includes isolating a CTC from a sample using a parylene microfilter device comprising a membrane filter having or consisting of a parylene substrate, which has an array of holes with a predetermined shape and size; and propagating said CTC in culture.

In still another aspect, the present invention provides a method for measuring telomerase activity in a single circulating tumor cell (CTC). The method includes isolating a group of CTCs from a sample using a parylene microfilter device comprising a membrane filter having or consisting of a parylene substrate, which has an array of holes with a predetermined shape and size; obtaining individual CTCs from the group of CTCs isolated from the sample; and determining telomerase activity of the CTC.

These and other objects, embodiments and advantages of the present invention will be more apparent to one of skill in the art from the following detailed description and Figures.

BRIEF DESCRIPTION OF THE DRAWINGS

FIGS. 3A-3D illustrate microfilter optimization and validation for capturing tumor cells. (A). Slot size and filtration pressure optimization using 1 ml whole blood. Left: Comparison of capture efficiency and viability generated by filters with different slot sizes. Center: Measurement of enrichment using filters with different slot sizes. Right: Comparison of capture efficiency and viability with various filtration pressures using 6 μm slot filter. (B) Cancer cells captured on microfilter from 1 ml whole blood. Shown are bright-field (left) and merged fluorescence (center) micrographs taken of the same field; yellow arrows (310) indicate live captured cancer cells, red arrows (320) indicate dead cancer cells, and black arrows (330) indicate PBMCs. Right: SEM micrograph of captured cancer cell. (C) Validation of cancer cell capture from a standard volume 7.5 ml specimen. Shown are capture efficiency (left), cell viability (middle) and enrichment (right). (D) On-filter (top) and off-filter (bottom) cell culture of captured PC-3 cells from human blood after 3 days and 6 days in RPMI complete medium.

FIGS. 8A to 8D illustrate telomerase activity measurement from single live cancer cells captured on microfilter. (A) Captured cells stained by PE-CD49b. (B) Matched bright field image. (C) Micropipette recovery of single cell. (D) Single cell telomerase activity assays.

DETAILED DESCRIPTION OF THE INVENTION

Figure 1:
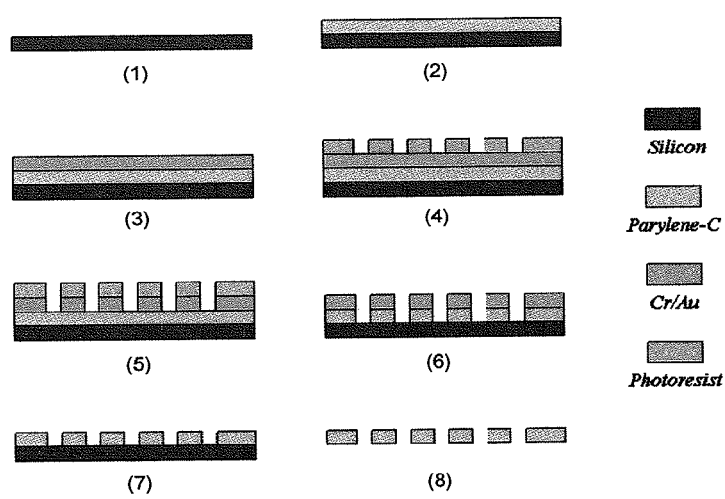
FIG. 1 illustrates a process for production of parylene microfilter according to an embodiment of the invention. (1) Silicon wafer as substrate; (2) 10 μm parylene-C coating; (3) Cr/Au deposition; (4) Lithography; (5) Metal etch; (6) Reactive Ion etching (RIE) of parylene; (7) Remove metal mask; (8) Release parylene membrane.

As used herein, the term "parylene" refers to a polymer having formulae I, II, and III or combinations thereof. The polymer can be a homopolymer, a copolymer, a polymer blend or combinations thereof. $R^1$, $R^2$, $R^7$ and $R^8$ are each independently H, alkyl, heteroalkyl, aryl or halogen. The alkyl can be a $C_1$-$C_6$ hydrocarbon radical. The halogen is Cl, F, Br, or I. Heteroalkyl is an alkyl substituent containing at least one heteroatom, such as O, S, N, Si or P.

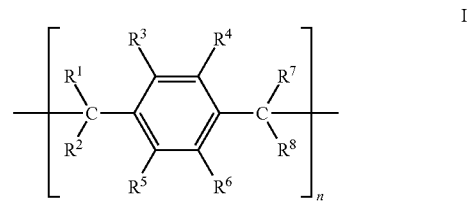

I

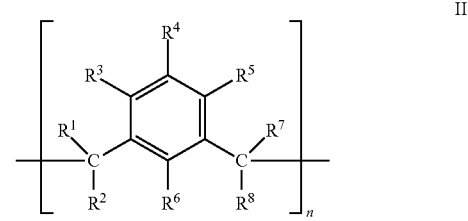

II

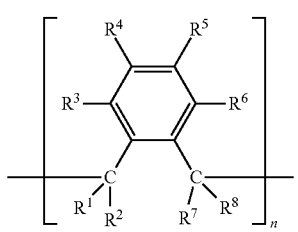

III $R^3$-$R^6$ are each independently H, alkyl, aryl, halogen, heteroalkyl, hydroxyl, amino, alkylamino, arylamino, aroylamino, carbamoylamino, aryloxy, acyl, thio, alkylthio, cyano, alkoxy. An alkyl group can be a substituted alkyl having up to 29 carbon atoms. A substituted alkyl can be mono- or polyunsaturated alkenyl or alkynyl radical having in each case up to 29 carbon atoms, i.e., a substituted $C_1$-$C_{29}$alkyl, $C_2$-$C_{29}$alkenyl or $C_2$-$C_{29}$alkynyl radical. Suitable substitutents are also cyclic radicals. The substituted alkyls can be methyl, ethyl, or propyl radical, carrying one or more identical or different radicals. Depending on the nature of the substitutents, these can be attached via a single or multiple bond or in a spiro form. Preferred substitutents are halogen, such as Cl, F, Br or I, amino, lower alkylamino, lower alkanoylamino, aroylamino, such as, in particular, benzoyl amino, hyroxyamino, hydroxyimino, lower alkoxyamino, aroxyamino, such as, in particular, phenoxyamino. Lower alkylthio includes $C_1$-$C_6$alkylthiols. Aryloxycarbonyl includes phenoxycarbonyl, benzyloxycarbonyl, hydroxyaminocarbonyl, aminoacylamino, carbamoyl, amidino. Aryoxy can be phenyloxy, aminocarbonyl-oxy, oxo, aminosulfonyl and lower alkylsulfonyl-amino. Heteroalkyl is an alkyl substitutent having one or more heteroatoms in the alkyl substitutents, in particular, mercaptoalkyl having up to 29 carbon atoms, aminoalkyl, phosphinoalkyl, haloalkyl, hydoxyalkyl or silylalkyl. Preferably, parylene has a structure represented by the formula I. In addition, preferred parylene also includes commercially available parylene, C, F, A, AM, N, and D.

As used herein, "polymerase" refers to an enzyme that catalyzes the polymerization of nucleotides (i.e., the polymerase activity). Generally, the enzyme will initiate synthesis at the 3'-end of the primer annealed to a polynucleotide template sequence, and will proceed toward the 5' end of the template strand.

As used herein, the term "primer" refers to a single stranded DNA or RNA molecule that can hybridize to a polynucleotide template and prime enzymatic synthesis of a second polynucleotide strand. A primer useful according to the invention is between 10 to 100 nucleotides in length, preferably 17-50 nucleotides in length and more preferably 17-45 nucleotides in length.

As used herein, "Quantitative PCR" or "QPCR" is defined as a polymerase chain reaction (PCR) process which monitors the kinetics of PCR for the quantification of DNA templates. When QPCR follows a reverse transcription reaction, it can be used for the quantification of RNA templates as well. The amplification of nucleic acid using qPCR is a transformation of a single strand of DNA into multiple copies.

As used herein, the term "monodispersed" refers to openings or holes on the membrane filter having substantially identical size, dimension and shape.

As used herein, the term "prognosis" defines a forecast as to the probable outcome of a disease, the prospect as to recovery from a disease, or the potential recurrence of a disease as indicated by the nature and symptoms of the case.

As used herein, the term "figure of merit" provides a measure of the efficiency of the filtration device. A large figure of merit number is an indication of higher filtration efficiency. Figure of merit is defined as the recovery rate divided by time. Recovery rate is defined as particles recovered divided by the total number of target particles. The time used in the calculation of figure of merit is the total processing time to conduct the testing. For example, in one embodiment, the parylene filter of the present invention has a figure of merit of greater than or equal to 890 and/or having a Young's modulus ≈4 GPa.

Parylene is a USP Class VI biocompatible polymer that can be deposited through a highly-conformal vapor deposition process. Types of parylene include parylene C, F, A, AM, N, and D. Of the three most common types of parylene shown below, parylene C is perhaps the most widely used in industry. The advantages of the use of parylene include its proven biocompatibility, its strength, elasticity and flexibility (e.g., Young's modulus ≈4 GPa), its conformal pinhole-free room-temperature deposition, its low dielectric constant (≈3) high volume resistivity (>$10^{16}$ Ω-cm), its transparency, and its ease of manipulation using standard microfabrication techniques such as reactive ion etching (RIE). In certain embodiments, the parylenes used in the present invention have Young's modulus of at least 4 GPa. Several research groups have used parylene C deposition as a method of creating a biocompatible, water-blocking seal around electrode arrays typically fabricated using a polyimide substrate. This is necessary because most polyimides have a moisture absorption that is more than an order of magnitude higher than that of parylene C. Some specialized polyimide films have lower moisture absorption, but they require high-temperature curing steps.

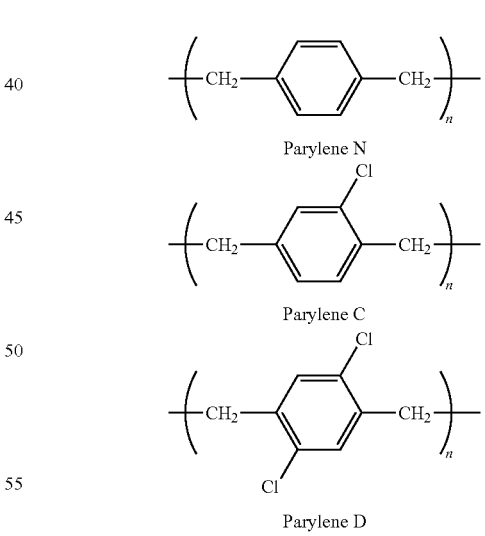

Parylene microfilters have found various applications. Parylene microfilter devices with predetermined geometric design have been described in U.S. Patent Publication No. 2006/0254972 as incorporated herein by reference. Use of parylene microfilters for various biological applications has been described in U.S. Patent Publication No. 2007/0025883 and PCT Patent Publication No. WO2006/116327, each of which is incorporated herein by reference. Parylene microfilters with a top and a bottom porous membranes for separating circulating tumor cells have been described in U.S. Patent Publication No. 2009/0188864, which is incorporated herein by reference.

In one aspect, the present invention provides a highly sensitive yet specific method for diagnosing cancer and/or predicting disease outcome and response to therapy by (i) isolating circulating tumor cells from body fluids, such as blood samples including peripheral blood samples using a parylene microfilter device, such as a parylene-C slot microfilter device, and (ii) determining the telomerase activity of the cells using a telomerase assay, such as a quantitative PCR-based detection. The parylene microfilter device includes a membrane filter having or consisting of a parylene substrate, which has an array of holes with a predetermined shape and size. In one embodiment, the method includes correlating the telomerase activity with malignant or metastatic potential. Advantageously, the captured cells retained normal morphology by scanning electron microscopy and can be readily manipulated, further analyzed, or expanded on or off filter. Remarkably, telomerase activity, a well-recognized universal cancer marker, is reliably detected by qPCR from as few as 25 cancer cells spiked into 7.5 ml whole blood and captured on microfilter. Moreover, significant telomerase activity elevation also was measured from patient blood samples, and even from single cancer cells lifted off the microfilter. Live CTC capture and analysis is fast and simple yet highly quantitative, versatile, and applicable to nearly all solid tumor types, making this suitable for cancer detection and characterization.

The parylene membrane filter comprises a plurality of holes of a predetermined geometric design formed in, and penetrating, the parylene membrane. The geometric design includes, for example, a size, a shape and density. In one embodiment, the design of the membrane is such that CTCs are selectively captured or retained by the membrane while other cells and materials in the blood pass through the membrane selected according to their size and shape. The efficiency of the membrane filter can be adjusted by changing the size, shape, density of the holes on the membrane and the pressure applied to the sample to be filtered. In some preferred embodiments, the filter of the present invention has a figure of merit up to 890. In other embodiments, the parylene membrane filter has a figure of merit between about 800 to about 890. In some preferred embodiments, the holes are monodispersed.

The predetermined geometric design is according to any one or more of the size, shape, density, uniformity, and arrangement of the holes in the parylene membrane. In some embodiments, the holes themselves can have rounded or sharp corners. The holes can be of a regular shape (e.g., circles, ovals, ellipses, squares, rectangles, symmetrical and unsymmetrical polygons, rods) or any other shape desired, including, but not limiting to, other irregular shapes. The holes can be of different sizes and shapes. The holes can all be of uniform size and/or shape. In some preferred embodiments, the holes may be limited to a predetermined range of sizes and/or shapes. In some embodiments, membrane filter has a hole shape selected from the group consisting of a circular, an elliptical, a symmetrical polygonal, an unsymmetrical polygonal, an irregular shape and combinations thereof. In a preferred embodiment, the holes have a rectangular shape and arranged uniformly. In some embodiments, the holes can be arranged in a uniform grid or array (e.g., one or more rows and/or columns, concentric circles, and the like). Preferably, holes are all of the same shape and size and may also be of uniform density or pattern on the membrane, aside from the edges.

The holes can be of any desirable size and shape which will determine the ability of a particle or cell of interest to pass through. For instance, in some embodiments, the holes may have a minimum or maximum cross sectional length of 1, 2, 3, 4, 5, 8, 10, 12, 14, 16, 18, 20, 24, 28, 30, 32, 36, 40, 45, 50 microns or more. In some embodiments, the holes are circles, ovals, rectangles or polygons. In some further embodiments, the circular holes have diameters of 2, 4, 8, 10, 14, 20, 30, 40, 50 microns or more. In other further embodiments, the holes are oval and have different lengths and widths which may be independently be selected from 2, 4, 6, 8, 10, 14, 20, 30, 40 or 50 microns. For instance, in some further embodiments, the holes may be circles from 6 to 10, 5 to 12, 10 to 20, 8 to 40, or 6 to 60 microns in diameter. In some preferred embodiments, the holes are rectangles whose dimensions are from 2 to 10 microns by 30 to 60 microns, from 4 to 9 microns by 35 to 50 microns, from 5 to 8 microns by 35 to 45 microns, or from 5 to 7 microns by 35 to 45 microns. In a more preferred embodiment, the holes are from 6 by 40 microns. In some embodiments, the minimum width of the rectangular holes is 1, 2, 4, 5, 5.5, 6, 6.5, 7, 8, 9 or 10 microns and the minimal length of the rectangular holes is 30, 31, 32, 33, 34, 36, 38, 39, 40, 41, 42, 43, 44, 45, 46, 48, 50 microns. In some embodiments, the width of the rectangular holes is 1, 2, 4, 5, 5.5, 6, 6.5, 7, 8, 9 or 10 microns and the length of the rectangular holes is 30, 31, 32, 33, 34, 36, 38, 39, 40, 41, 42, 43, 44, 45, 46, 48, 50 microns. In some embodiments, of any of the above the maximum length of the hole is 50, 60, 70, 80, 90, 100 microns or 200 microns.

The holes may also be defined according to their cross sectional area and/or shape. The shapes can be as any described above, preferably, the shapes are rectangle. In some embodiments, the cross sectional areas range from about 1 to 1000 square microns, 1 to 10 square microns, 10 to 100 square microns, 25 to 500 square microns, 50 to 400 square microns, 75 to 150 square microns, 75 to about 500 square microns or 200 to 1000 square microns. In certain embodiments, the cross sectional areas range from 50 to 300 square microns, 100 to 200 square microns, 200 to 240 square microns, 150 to 300 square microns, 200 to 280 square microns or 200 to 400 square microns. In one embodiment, the holes have a slot/rectangular shape and a cross sectional area of 240 square microns. In any of the above, the holes can be monodispersed. In any of the above, the parylene membrane filter can have a figure of merit up to 890, and preferably from 800 to 890.

In some embodiments, the parylene membrane filter has a hole density of from 1 to 40,000, 1,000 to 40,000, 5,000 to 40,000; 6,000 to 40,000, 7000 to 40,000, 10, 000 to 40,000; 10,000 to 30,000; 20,000 to 30,000; 20,000 to 40,000; or 30,000 to 40,000 holes per square millimeter. In certain instances, the parylene membrane filter has an array of rectangle holes with a hole density from 1 to 1000, 1 to 900, 1 to 850, 1 to 800, 1 to 700, 1 to 600, 100 to 1000, 300 to 1000, 500 to 900, 400 to 800, or 600 to 900 holes per square millimeter. In one instance, the parylene membrane filter has an array of rectangle holes with a hole density of 100, 200, 300, 400, 500, 600, 700, 800, 850, 900 or 1000 holes per square millimeter. In certain embodiments, the hole density is at least 1, 10, 100, 200, 300, 400, 500, 600, 700, 800, 900, 1000, 2000, 3000, 4000, 5000, 6000, 7000 or 8000 holes per square millimeter. In a preferred embodiment, the parylene membrane filter has 30401 or more holes per 36 square millimeters. Such hole densities depend in part upon the sizes of the holes, with smaller holes allowing for greater densities. The densities can be adjusted so as to insure that the holes do not fuse together during manufacture and the strength of the parylene membrane remains suitable. A thicker membrane can be used to strengthen the membrane at higher hole densities.

In certain embodiments, the number and size of the holes affects the rate at which a sample can pass through the membrane and the strength of the membrane. The density of the holes is typically range from 1,000 to 40,000 holes per square millimeter. The plurality of holes can provide an opening area ratio of from 4% to 60%, including ranges from 4% to 25%, 5% to 25%, 10% to 25%, 15% to 30%, 5% to 45%, 10% to 50%, 15% to 45%, 20% to 40%, 25% to 50%, and 45% to 60%. In some embodiments, the area opening ratio is at least 1%, 2%, 4%, 5%, 8%, 10%, 12%, 13%, 14%, 15%, 17%, 18%, 19% or 20%. In one embodiment, the area opening ratio is 18%.

In some embodiments of the above, the parylene membrane filter is from 0.5 to 20 microns thick. In some preferred embodiments, the membrane is at least 1, 2, 3, 4, 5, 6, 7, 8, 9, 10, 11, 12, 13, 14, 15 or 16 micron thick. In other embodiments, the membrane filter is from 1 to 20 microns thick, in more preferred embodiments, the membrane filter is from 1 to 4, 5 to 10, 5 to 15, 8 to 15 or 10 to 20 microns thick. In one embodiment, the parylene membrane filter has a thickness of 10 microns. The thickness of the membrane filter is a compromise between membrane strength and flow resistance through the membrane. Accordingly, as increasing hole density reduces membrane strength, membranes having a greater number of holes typically require a thicker membrane than membranes having a fewer number of the same holes.

Figures 2A, 2B, 2C:
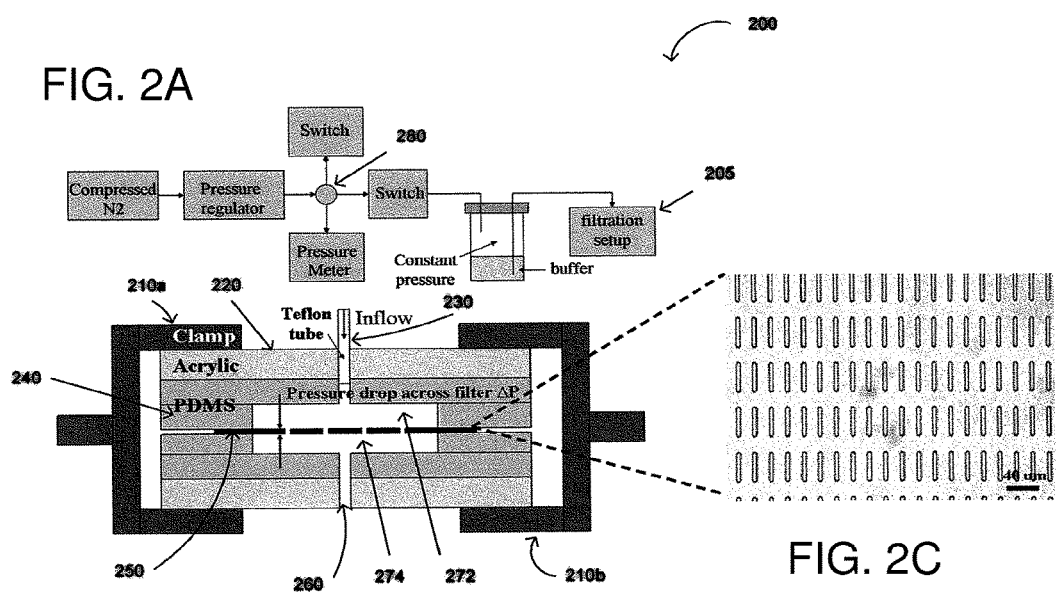
FIGS. 2A-2C illustrate the experimental setups according to an embodiment of the invention. A. Constant pressure fluid delivery system. B. Cross-sectional view of the filtration setup. C. Top view of slot filter. Each filter contains 30401 slots per 36 square millimeter. The thickness of the parylene-C membrane filter is 10 μm.

In some embodiments, a constant pressure can be applied to the sample to facilitate the filtration process, preferably, a constant low-pressure is applied to the sample. The pressure can range from 0.01 to 0.5 psi, preferably from 0.05 to 0.4 psi, more preferably from 0.1 to 0.3 psi and even more preferably from 0.1 to 0.25 psi. In one embodiment, the constant pressure is 0.1, 0.11, 0.12, 0.13, 0.14, 0.15, 0.16, 0.17, 0.18, 0.19, 0.2, 0.21, 0.22, 0.23, 0.24 or 0.25 psi. In another embodiment, a maximum constant pressure applied to the sample is 0.1, 0.11, 0.12, 0.13, 0.14, 0.15, 0.16, 0.17, 0.18, 0.19, 0.2, 0.21, 0.22, 0.23, 0.24, 0.25, 0.36, 0.27, 0.28, 0.29 or 0.3 psi. In one embodiment, the pressure applied to the sample is generated by an electrokinetic, for example, electroosmosis, and a ratchet pump. In yet another embodiment, the pressure is generated using pneumatic or magneto hydrodynamic pumps. In yet a further embodiment, the pressure applied to the fluid is generated by a mechanical device. One example of a useful mechanical pressure generating device is a screw-type pumping device or a peristaltic pump. In a preferred embodiment, the pressure is generated through a compress gas source. Exemplified gases include nitrogen, argon, helium, air, carbon dioxide or oxygen. The pressure is preferably applied through a pressure delivery system, for example, as depicted in FIG. 2A.

The filtration sample can be any body fluid containing tumor cells. For instance, the sample can be a blood sample from a mammal. In one embodiment, the sample is a peripheral blood sample obtained from a patient.

In some embodiments, the invention provides a method for determining the isolated CTCs using a telomerase activity, such as determined by an assay. The method further provides correlating the telomerase activity with malignant or metastatic potential. Telomerase is a specialized reverse transcriptase that through a transformation synthesizes telomeric DNA and thus contributes to the maintenance of functional telomeres. In most cancers and in stem cells of renewal tissues, telomerase activity levels generally correlate with the proliferation state of the cells. The presence of the enzyme is almost always required for unlimited proliferation (immorality) whereas its absence may dictate a finite lifespan (senescence). In fact, telomerase activity is a well-recognized cancer marker in >90% of human malignancies (Streutker, C. J., et al., *Pediatr Dev Pathol* 2001; 4:62-7) and therefore is ideally suited to the microfilter, which can capture CTCs across all tumor types regardless of surface markers. Telomerase activity also constitutes a uniquely "functional" assay which reflects the presence of live cancer cells, in contrast to other CTC readouts such as cancer-specific gene products or mutations that can be falsely amplified by qPCR from dead cells or cellular debris. Moreover, qPCR-TRAP can amplify the telomerase activity signal through a transformation from as few as one cancer cell, raising the prospect of applying CTC-telomerase not only as a prognostic or predictive biomarker, but also as a method for early screening and detection of occult malignancy. The versatility and wide applicability of CTC live-capture and analysis make this a powerful new strategy for the study of cancer dissemination and for the advancement of patient care.

It is known in the art that tumor samples can be assayed by PCR-based telomeric repeat amplification protocol (TRAP) (Holt, S. E., et al. *Methods Cell Sci* 1996, 18, 237-248). TRAP is a two-step process. A cell or tissue sample is lysed with a buffer containing detergent, and an aliquot of lysate is mixed with a reaction solution containing elements for the two-step process of telomerase product formation and amplification. In the first step, the telomerase substrate and dNTPs within the reaction solution are used for the addition of telomeric repeats by telomerase if it is present within the sample lysate (represented as a ladder on acrylamide gels). This step involves a transformation. In the second step, forward and reverse primers for these products are used for amplification. The amplification verifies a transformation. Real time quantitative TRAP allows a more rapid, high-throughput, quantitative analysis of telomerase activity in cell or tissue samples; therefore, this assay is optimal for clinical use (Elmore, L. W. et al. *Diagn. Mol. Pathol.* 11, 177-85, (2002); and Jakupciak, J. P. *Expert Rev. Mol. Diagn.* 5, 745-53 (2005)). Analysis of Q-TRAP described in this protocol is based on standard real-time PCR analysis, which uses a relative standard curve method. The cycle threshold (Ct) of an unknown sample is compared to a standard curve to quantify the relative amount of telomerase activity, which can then be normalized to the standard.

In one embodiment, the determination of the telomerase activity includes obtaining a telomerase extension product; and amplifying the extension product by a quantitative PCR-based telomerase repeat amplification protocol assay. In one instance, the telomerase extension product is obtained by lysing the isolated circulating tumor cell to produce a cell lysate; and mixing the cell lysate with an oligonucleotide that is a substrate for telomerase extension to obtain an extension product.

In another aspect, the present invention provides a method for detecting and quantifying the telomerase activity of a circulating tumor cell. The method includes isolating the circulating tumor cell from a sample using a parylene microfilter device comprising a membrane filter consisting of a parylene substrate having an array of holes with predetermined dimensions and sizes; and determining the telomerase activity of the isolated circulating tumor cell using a quantitative PCR telomerase activity assay. In one embodiment, the sample is a peripheral blood sample. Preferably, the isolated cells are alive. In some embodiments of any of the above, the holes have a rectangular shape. The width of the rectangular holes is from 1 to 10 microns, preferably 2 to 8 microns, more preferably 4 to 7.5 microns and even more preferably 5 to 7 microns; and the length of the rectangular holes is from 30 to 50 microns, preferably 35 to 45 microns, more preferably 37 to 42 microns and even more preferably 38.5 to 41.5 microns. In one embodiment of any of the above, the rectangular hole size is 5.5 to 6 by 39.5 to 40 microns. In one instance the rectangular hole size is 5.5 by 40 microns or 6 by 40 microns. In some embodiments, the rectangular holes have a width of 1, 2, 4, 5, 5.5, 6, 6.5, 7, 8, 9 or 10 microns and a length of 30, 31, 32, 33, 34, 35, 36, 37, 38, 39, 40, 41, 42, 43, 44, 45, 46, 47. 48, 50 microns. In other embodiments, the rectangular holes have a minimum width of 1, 2, 4, 5, 5.5, 6, 6.5, 7, 8, 9 or 10 microns and a minimum length of 30, 31, 32, 33, 34, 35, 36, 37, 38, 39, 40, 41, 42, 43, 44, 45, 46, 47. 48, 50 microns. In yet other embodiments, the rectangular holes have a maximum width of 1, 2, 4, 5, 5.5, 6, 6.5, 7, 8, 9 or 10 microns and a maximum length of 30, 31, 32, 33, 34, 35, 36, 37, 38, 39, 40, 41, 42, 43, 44, 45, 46, 47. 48, 50 microns. In some embodiments of any of the above, the sample is passed through the parylene filter under a constant-low-pressure. The pressure can range from 0.01 to 0.5 psi, preferably from 0.05 to 0.4 psi, more preferably from 0.1 to 0.3 psi and even more preferably from 0.1 to 0.25 psi. In one embodiment, the constant pressure is 0.1, 0.11, 0.12, 0.13, 0.14, 0.15, 0.16, 0.17, 0.18, 0.19, 0.2, 0.21, 0.22, 0.23, 0.24 or 0.25 psi. In another embodiment, a maximum constant pressure applied to the sample is 0.1, 0.11, 0.12, 0.13, 0.14, 0.15, 0.16, 0.17, 0.18, 0.19, 0.2, 0.21, 0.22, 0.23, 0.24, 0.25, 0.36, 0.27, 0.28, 0.29 or 0.3 psi.

In yet another aspect, the present invention provides a method for enriching circulating tumor cells. The method includes passing a sample containing a circulating tumor cell through a parylene microfilter device comprising a membrane filter consisting of a parylene substrate having an array of holes with a predetermined shape and size; and capturing said circulating tumor cell on the membrane filter, wherein the enrichment of circulating tumor cells is greater than 200, 300, 400, 500, 600, 700, 900, 1000, 1100, 1200, 1300, 1400, 1500 or 2000 fold. In one embodiment, the sample is filtered under a constant-low-pressure. In another embodiment, the method provides a greater than 90% capture efficiency and greater than 90% cell viability. In some preferred embodiments, the method provides a greater than 91, 92, 93, 94, 95, 96, 97, 98 or 99% capture efficiency. In other preferred embodiments, the method provides a greater than 91, 92, 93, 94, 95, 96, 97, 98 or 99% cell viability. The sample, the parylene filter, the shape and size of the array of holes and the pressure are as defined in any of the embodiments above. In a preferred embodiment within any of the above embodiments, the holes have a rectangular shape with the dimension as described in any of the above embodiments.

In still another aspect, the present invention provides a system for isolating a circulating tumor cell. The system includes a parylene microfilter device comprising a membrane filter consisting of a parylene substrate having an array of holes with a predetermined shape and dimension; and a constant pressure delivery system coupled to the parylene microfilter device for maintaining a constant pressure. The sample, the parylene filter, the shape and size of the array of holes and the pressure are as defined in any of the embodiments above. In one embodiment, the pressure is between 0.01 and 0.3 psi. In a preferred embodiment, the holes have a rectangular shape with the dimension as described in any of the above embodiments.

In another aspect, the present invention provides a method for measuring mRNA expression levels of a gene of interest in a circulating tumor cell (CTC). The method includes isolating a CTC from a sample using a parylene microfilter device comprising a membrane filter consisting of a parylene substrate having an array of holes with a predetermined shape and size; and measuring the mRNA expression levels of the gene in the CTC. In some embodiments, the mRNA expressions, tumor markers, are proteins including, but not limiting to, Alpha-fetoprotein (AFP), Beta-2-microglobulin (B2M), Beta-HCG, Bladder tumor antigen (BTA), CA 15-3, CA 27.29, CA 125, CA 72-4, CA 19-9, Calcitonin, Carcinoembryonic antigen (CEA), Chromogranin A, Epidermal growth factor receptor (EGFR), Hormone receptors, HER2 (also known as HER2/neu, erbB-2, or EGFR2), Human chorionic gonadotropin (HCG), Immunoglobulins, Neuron-specific enolase (NSE), NMP22, Prostate-specific antigen (PSA), Prostatic acid phosphatase (PAP), Prostate-specific membrane antigen (PSMA), S-100, TA-90 and Thyroglobulin. Examples of cancers linked to the above markers include, but are not limited to, bladder cancer, breast cancer, colorectal cancer, gestational trophoblastic disease, liver cancer, lung cancer, melanoma skin cancer, multiple myeloma, ovarian cancer, pancreatic cancer, prostate cancer, stomach (gastric) cancer, testicular cancer, seminoma and non-seminoma. Examples of oncogenes found in tumors include, but are not limited to, BRCA1, BRCA2, RAS (also called HRAS), BCR-ABL, MYC, MSH2. MSH6, MLH1, CDKN2, HPC1, erb-B2, PI3-K, AKT and β-catenin.

In another aspect, the present invention provides a method for staining a circulating tumor cell (CTC). The method includes isolating a CTC from a sample using a parylene microfilter device comprising a membrane filter consisting of a parylene substrate having an array of holes with a predetermined shape and size; and staining the CTC with a dye or an antibody conjugated to a dye. Various dyes and antibodies conjugated to a dye known in the art can be used for staining the CTCs. Exemplary dyes include, but are not limited to, Acridine orange, Bismarck brown, Carmine, Coomassie blue, Crystal violet, DAPI, Eosin, Ethidium bromide, Acid fuchsine, Haematoxylin, Hoechst stains, Iodine, Malachite green, Methyl green, Methylene blue, Neutral red, Nile blue, Nile red, Osmium tetroxide (formal name: osmium tetraoxide), Rhodamine and Safranin.

The invention also provides a method of expanding or propagating a filter-captured cell in culture. The method includes isolating a CTC, such as a viable CTC from a sample using a parylene microfilter device, which comprises a membrane filter consisting of a parylene substrate having an array of holes with a predetermined dimension and size; and propagating the cell in culture either on filter or by washing them into a culture dish. The conditions for culturing a cell are well known to persons of skill in the art. For example, the cells can be maintained in an incubator at 5% $CO_2$ and 37° C.

In yet another aspect, the present invention provides a method for measuring telomerase activity in a single circulating tumor cell (CTC). The method includes isolating a group of CTCs from a sample using a parylene microfilter device comprising a membrane filter consisting of a parylene substrate having an array of holes with a predetermined shape and size; obtaining individual CTCs from the group of CTCs isolated from the sample; and determining telomerase activity of the CTC. In one embodiment, a micropipette is used to recover individual CTCs from a group of CTCs isolated from a sample.

FIG. 1 illustrates a parylene-C microfilter membrane fabrication process. The filter fabrication process started from depositing, for example, a 10 μm-thick parylene-C layer on prime silicon wafer. Parylene-C layer with other thickness as described above can also be used. A metal layer, either Cr/Au or Al, was then deposited using a thermal evaporator, followed by lithography and wet-etching patterning. Parylene-C was patterned by Reactive Ion Etching (RIE) using the metal as the mask. Finally, the patterned parylene-C membrane was peeled off from the silicon substrate.

FIG. 2 illustrates a parylene filter device for capturing viable CTCs. The microfilter device is capable of enriching and trapping CTCs with unprecedented efficiency based on the size and deformability differences between CTC and blood cells. Size based filtration method is an efficient way to enrich CTCs (15-30 μm in diameter) from RBCs (6-9 μm) and WBCs (5-16 μm). Advantageously, the slot size is 5.5×40 μm, which allows most RBCs and WBCs to deform and pass through, but can successfully trap CTCs. The parylene filter device system consists of a constant-pressure driven fluid delivery system coupled to a parylene filter assembly 205 (FIG. 2B). The filter device includes a parylene membrane 250 mounted inside a housing. The housing can adopt a variety of sizes and shapes, which include, but is not limited to, tubular, spherical and cubical shapes. In one embodiment, the housing is made of a top chamber 272 having an insertion port connected to a tubing 230 and a bottom chamber 274 having an exit port 260. Various materials can be used for the construction of the chambers. The materials include, but are not limited to, polysiloxane, polycarbonate, polyacrylate, polyethylene, polystyrene, polysaccharides and copolymers and combinations thereof. In one embodiment, the material used for construction of the chambers is polydimethylsiloxane (PDMS). In one embodiment, the top chamber, the bottom chamber and a parylene membrane are clamped together by two pairs of clamps 210a and 210b. The clamps can be made of polyacrylate, polyketone, polystyrene, polypropylene and the like or an engineering material, which includes, but is not limited to, a polyketone, a polysulfone, a polysulfide, a polyimide or a polyetheretherketone (PEEK). The clamps are held together by suitable means, such as bolts, fasteners, screws, latches, links, joints, locks or unions. The parylene membrane filter 250 has an array of rectangular (slot) holes. Compared to the circular pores, slots allow easier deformation of blood cells in the slot longitudinal direction, which facilitates easier passage of normal blood cells. In addition to the slot design, the large fill factor also greatly reduces the flow resistance during filtration.

In FIG. 2A, the constant-pressure driven fluid delivery system includes a nitrogen tank, a pressure regulator, a pressure gauge, a fine pressure control needle valve 280, switches and sample. The fine pressure control valve is capable of driving the sample with an accuracy of ±0.01 psi. In previous filtration approaches, samples were driven by hand-push, syringe pump or other means. Although a near-constant flow rate could be achieved, the pressure drop ($\Delta P$) across the filter increased when the filter was gradually clogged. Advantageously, the constant-pressure-driven fluid delivery system is able to keep a constant $\Delta P$ during filtration. Not being bound by any theory, the slot filter's reduced flow resistance then allows a low and constant $\Delta P$ to filter out CTCs, which minimizes the forces exerted on the cells, and hence results in high viability. Surprisingly, under a constant-low-pressure driven system, the parylene filters with a rectangular hole shape and predetermined hole size have been found to provide high CTC capture efficiency (>90%), high cell viability (>90%) and high CTC enrichment (>200 fold).

FIG. 3A shows the capture efficiency, viability and enrichment of CTCs using parylene filters having sever different slot sizes. Preferred slot width is about 6 microns for prostate cancer cells. High pressures reduce capture efficiency and cell viability. Low pressure is critical for live cell capture. Preferred drive pressure is about 0.13 psi. The low pressure preserves the morphology of captured cells (FIG. 3B) and allows fast filtration. For example, filtration of 1 mL whole blood using the system of the present invention is done in less than 5 minutes, a capture rate that is 12 times faster than that of other recently-published microfluidic platforms (Nagrath, S. et al., *Nature* 2007; 450:1235-9). Using the filtration system of the present invention, a 1500 fold enrichment of CTCs is observed (FIG. 3C). In some embodiments, the filtration system of the present invention provides enrichment of CTCs for at least 200, 300, 400, 500, 600, 800, 1000, 1200, 1500, 1600, 1800 or 2000 fold.

As shown in FIG. 3D, the captured cancer cells can be expanded in culture either directly on filter or by first washing them into a culture dish (FIG. 2D). Notably, the parylene microfilter provides a biocompatible environment for cancer cell adherence and growth or alternatively could release the captured cells without damaging them. These properties would allow potential expansion and study of captured CTCs for cancer phenotyping and treatment selection. The parylene slot filters have the advantages of biocompatibility and capability of release captured cells. FIG. 3D shows that for on-filter culture, even without any surface pre-treatment, cancer cells are able to adhere and proliferate on the filter surface. For off-filter culture, trapped cells are first released and collected from the filter, by multiple rinses or reverse flow (passing PBS from backside), and then cultured in petri-dish.

Figure 4:
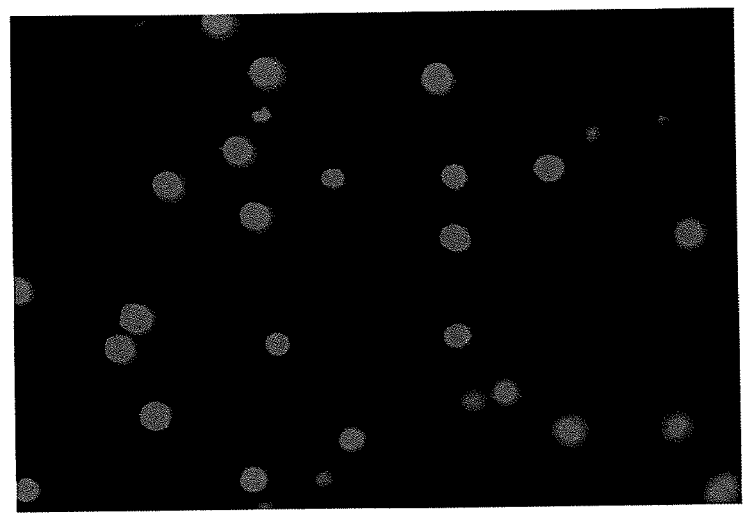
FIG. 4 shows an image of captured pre-stained tumor cells on filter spiked into blood (20×).

FIG. 4 shows that cancer cells can be successfully isolated from blood using the parylene-C based slot microfilter. For example, prostate tumor cells DU145 were pre-stained with carboxyfluorescein succinimidyl ester (CFSE). Tumor cells were then counted and spiked into blood. The buffy coat layer (containing nucleated cells) was extracted by Ficoll gradient centrifugation, and these cells were filtrated by the slot filter using constant pressure driving system. FIG. 4 shows captured tumor cells on filter. Tumor cells were still alive and fluorescence dye was kept inside the intact membrane (see also FIGS. 3B and 3C).

Figure 5:
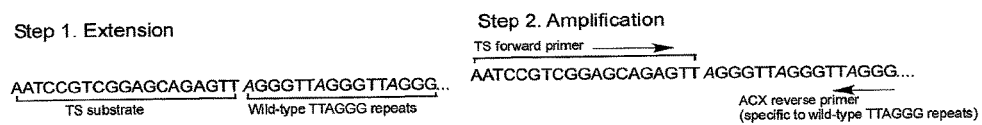
FIG. 5 illustrates a strategy for quantitative PCR detection of telomerase activity according to one embodiment of the invention (SEQ ID NOS:1 and 2).
Figure 6A:
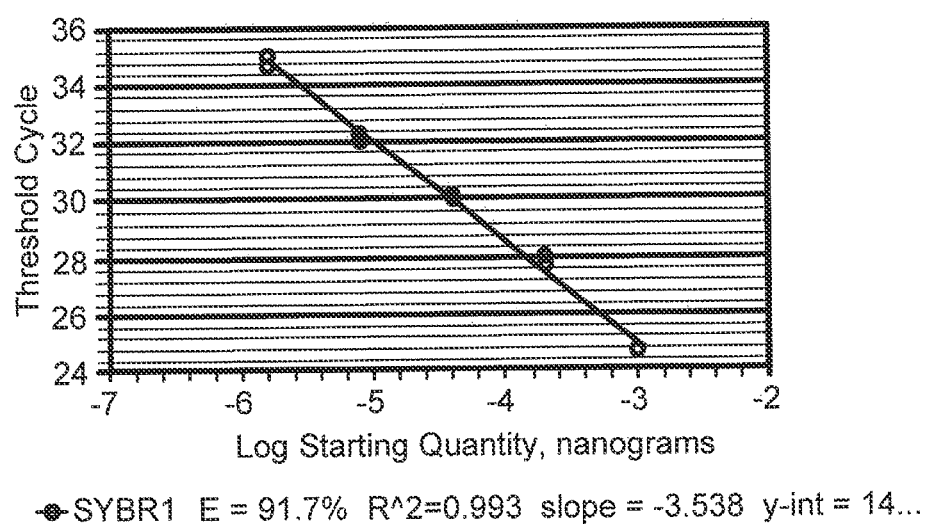
FIGS. 6A to 6B illustrate qPCR-based telomere repeat amplification protocol (qPCR-TRAP). A. Standard dilution curves comparing the log of cell numbers (from which telomerase-containing protein lysates are extracted) to the resulting qPCR threshold cycle (Ct, the amplification cycle at which the telomeric products made by telomerase are detected). The more telomerase activity, the fewer qPCR amplification cycles required for detection of products (hence lower Ct). The cell line is LNCaP; cell numbers and the corresponding Ct's are indicated in the table. B. Histogram of qPCR-based telomerase activity of preparations consisting of various ratios of LnCaP cells and peripheral blood mononuclear cells (PBMCs); cancer cell telomerase activity is detectable above the PBMC background at a ratio of 1:1000.
Figure 6B:
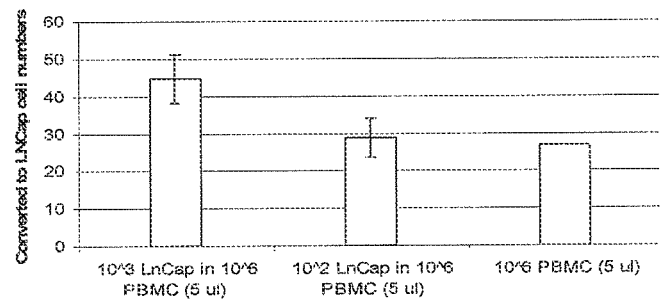

Compared to normal cells, most cancer cells have higher telomerase activity, which directly indicates their malignant/metastatic potential (see, Fizazi, K. et al., *Annals of Oncology*, vol. 18, pp. 518-521, 2007; and Herbert, B. S. et al., *Nature Protocols*, vol. 1, pp. 1583-1590, 2006). Moreover, most cancer cells possess very high telomerase activity that correlates directly with malignant/metastatic potential (see, Shay, J. W. et al. *Eur. J. Cancer* 1997, 33, 787-791; and Meeker, A. K. et al. Urol Onc. 2006, 24, 122-130), a property which has demonstrated prognostic utility when measured in body fluids and tumor specimens (see, Carey, L. A. et al., *J Clin Oncol* 1999, 17, 3075-81; Oishi, T. et al., *Obstet Gynecol* 1998, 91, 568-71; Poremba, C. et al., *J Pathol* 2002, 198, 181-89; Tomoda, R. et al., *Cancer* 2002, 95, 1127-33; and Sanchini, M. A. et al., *JAMA* 2005, 294, 2052-56). Hence, the measurement of telomerase activity of CTCs is important for cancer metastasis study. Telomerase activity is preferably measured from viable cells. Although the telomerase activity of individual whole blood cell (WBC) is low, without an efficient enrichment, the telomerase activity from all the WBCs may still add high background noise to the telomerase activity of CTCs. The parylene filtration system of the present invention provides enrichment of CTCs and allows picking up a single cancer cell using micropipette from the enriched viable cancer cells on the filter and isolating the single cancer cell and obtaining its telomerase activity by sensitive quantitative PCR (qPCR). qPCR-based detection of telomerase activity involves a two-step assay: (1) The microfilter-trapped CTCs are lysed, and the cell lysate (which contains telomerase) is mixed with an oligonucleotide that serves as a substrate for telomerase extension, the extension product is a result of a transformation; and (2) The extension product is then amplified by quantitative PCR (see, FIG. 5 and Herbert, B. S. et al., Nat Protoc 2006, 1, 1583-90).

Figure 7A:
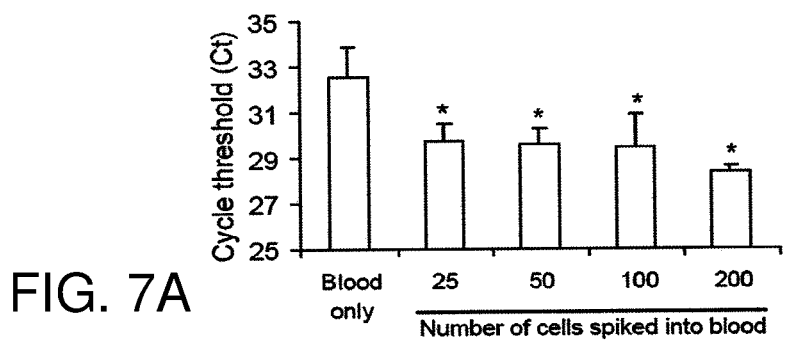
FIGS. 7A to 7E illustrate qPCR-based detection of telomerase activity from live cancer cells captured on slot microfilter. (A) Telomerase activity detected from 7.5 ml blood samples spiked with a range of cancer cell numbers or blood only (p=0.01 for each sample compared with blood-only sample). (B) Linear correlation of Ct values with the number of spiked cells. Results in all histograms are means of triplicate independent experiments. (C) Telomerase activity of patient samples versus healthy donor controls. The line in healthy donors indicates the calculated normal cut-off value of Ct at 33; patient samples falling within positive range (Ct<cut-off value) are boxed. (D) Serial filtration to internally control for PBMC background telomerase activity on 6 positive patient samples (p=0.029) (E) Serial filtration to internally control for PBMC background telomerase activity on healthy donor samples (p=0.5).
Figure 7B:
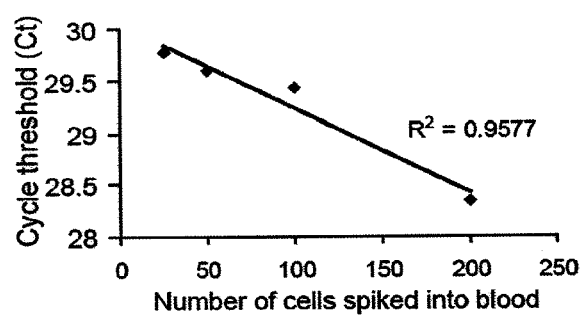
Figure 7C:
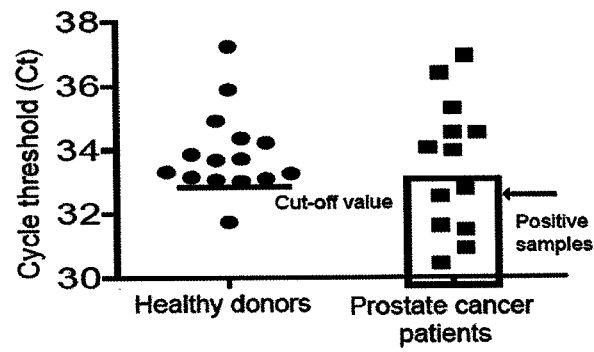

Experiments were performed using cancer cells introduced into freshly-drawn whole blood and showed that telomerase signal could be reliably obtained and correlated to the number of cancer cells introduced (FIGS. 7A and 7B). FIG. 7A shows a linear correlation between the number of cancer cells seeded and resulting telomerase activity. FIG. 7B shows the PCR threshold cycle value (Ct) value is inversely proportional and linearly correlated with the number of spiked cells. In one embodiment, pre-determined numbers of cancer cells are "spiked" into freshly collected 7.5 ml blood samples from healthy volunteers. The blood containing the cancer cells are Ficoll centrifuged to separate the "buffy coat" (containing nucleated cells) from red blood cells, and the buffy coat contents is passed through the parylene-C slot microfilter to separate and trap the cancer cells from white blood cells. The microfilter trapped cells are lysed, and the cell lysates are subjected to qPCR telomerase detection. The CTCs that can be captured and detected by the methods of the present invention include, but are not limited to, prostate cancer cells, lung cancer cells, breast cancer cells, colorectal cancer cells, bladder cancer cells, endometrial cancer cells, kidney cancer cells, leukemia, melanoma, skin cancer cells, thyroid cancer cells, non-hodgkin lymphoma, pancreatic cancer cells and hepatocellular carcinoma. This is surprising in view of the fact that that hepatocellular carcinoma cannot be assayed using EpCAMs.

Figure 7D:
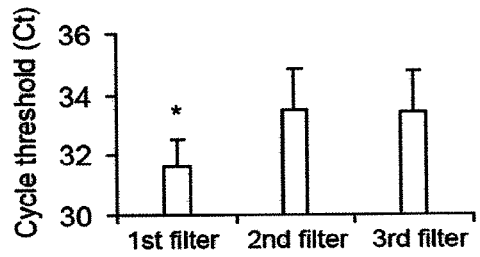
Figure 7E:
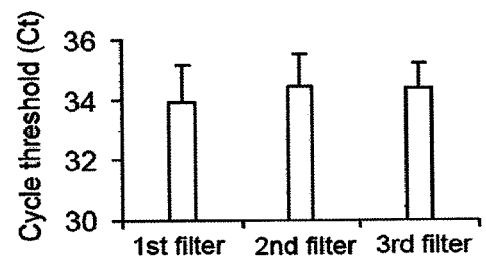

As shown in FIGS. 7D and 7E, when the CTC telomerase platform was applied to clinical samples from men with metastatic prostate cancer versus healthy controls, 5 of 12 patient blood samples had significant telomerase activity elevation, with an average Ct of 31.4. In contrast, 0 of 6 healthy donor samples had telomerase activity elevation, with an average Ct of 33.4; hence, the positive patient samples possessed approximately 4-fold telomerase activity relative to the healthy donor samples.

The telomerase activity assay can be controlled to reflect only the captured CTCs and not the background peripheral blood mononuclear cells (PBMCs), which may vary between patients or even within one patient over time. For example, this was accomplished by passing each sample through 3 microfilters in series, and performing qPCR-TRAP on lysates from each microfilter. As expected (FIG. 8B), serial filtration of 7.5 ml of blood spiked with 20 cancer cells yielded high telomerase activity from the first filter (Ct=29.5, representing captured CTCs), and significantly lower activity from the 2nd and 3rd filters (33.5 and 33.4, respectively, representing background PBMCs). This approach enables telomerase activity readings to be internally controlled for PBMC background.

FIG. 8A-8C show the measured telomerase activity of both recovered cancer cells and control cells. Different Ct values (threshold cycle) mean the telomerase activity varied among different cells. Higher telomerase activity (lower Ct) is associated with a more aggressive, metastatic cancer phenotype. For example. PC3 cancer cells were captured from whole blood on microfilter, localized by immunofluorescent staining (PE-conjugated anti-CD49 antibody), and recovered individually using a micropipette mounted onto a XYZ manipulating stage (FIG. 8C). Single cancer cells were deposited in CHAPS lysis buffer and subjected to qPCR-TRAP, which yielded a significantly elevated telomerase activity level relative to negative controls. Slot microfilter live-capture can thus be used to assay telomerase activity or other biological or enzymatic processes from viable single CTCs (FIG. 8D).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Material and Methods

Cell Culture:

PC3 and DU145 Cancer Cell Lines were Maintained in RPMI/10% FBS at 37° C.

Example 1

Production of Parylene-C Slot Microfilter System

Filter Fabrication

As shown in FIG. 1, a parylene-C membrane filter was prepared according to the following processes.

1. Prime silicon wafer as substrate.
2. Coating of 10 μm parylene-C.
3. Ebeam deposition of 10 nm Cr and 200 nm Au.
4. Spin-coating of AZ1518 photoresist and lithography to form pattern.
5. Wet-etching of metal layers using photoresist as mask.
6. Reactive Ion Etching (RIE) of parylene-C to form slots (an array of 30,401 slots), using
    metal as mask.
7. Strip off metal mask.
8. Parylene-C membrane is peeled off from silicon substrate.

Constant Pressure Fluid Delivery System

Pressure from a nitrogen tank was reduced below 1 psi by a two-stage regulator (FIG. 2) and further down regulated accurately by adjusting a needle valve to 0.1-0.13 psi. A 15 ml conical tube containing the sample was connected as a reservoir. The filter was sandwiched between two thin pieces of polydimethylsiloxane (PDMS) with wells to form a chamber, which was then clamped between PDMS/acrylic jigs from top and bottom to form a sealed system (FIG. 2).

Example 2

Use of Parylene-C Slot Microfilter-Based Enrichment of Blood CTCs

Capture Efficiency, Cell Viability and Enrichment:

PC3 and DU145 human prostate cancer cell lines were stained with Calcein-AM fluorescent dye, and 10 cells were spiked into 1 ml human blood obtained from healthy volunteers. After filtration, captured cells were co-stained with Propidium iodide (PI) on filter and counted under a fluorescent microscope (Zeiss Imager.Z1 microscope) with Axiovision software. Viable Calcein-AM-retaining cells were fluorescent green while dead cells were fluorescent red by PI.

Capture efficiency was calculated as:

$$\text{Capture efficiency (\%)} = \frac{\text{cancer cells (green + red) on filter}}{\text{cancer cells spiked into blood}} \times 100$$

Cell viability was calculated as:

$$\text{Cell viability (\%)} = \frac{\text{green fluorescent cells}}{\text{total captured cancer cells (green + red)}} \times 100$$

Enrichment was determined by staining and counting the PBMCs remaining on filter with Acridine Orange and was calculated as:

$$\text{Enrichment (fold)} = \frac{(\text{cancer cells}/PBMCs)_{\text{on filter post-filtration}}}{(\text{cancer cells}/PBMCs)_{\text{original blood sample}}}$$

7.5 ml blood samples were processed similarly but with the addition of Ficollpaque gradient centrifugation at 900 g for 30 min and resuspension in 2 ml of PBS.

Patient Specimen Collection and Processing:

7.5 ml blood samples were drawn from patients with metastatic prostate cancer under an IRB-approved protocol, as well as from healthy volunteer controls. All specimens were collected into EDTA K2 vacutainer tubes and processed within 24 hours of collection Sample Processing Blood Samples were processed as follows:

1. 7.5 ml blood is drawn from patient into ethylenediaminetetraacetic acid EDTA (K2) tube (BD #366643).
2. Dilute the blood with 7.5 ml 1×PBS solution in a 50 ml conical tube.
3. Add 4 ml of Ficoll-Paque (GE healthcare) into 15 ml conical tubes. Carefully layer 7.5 ml of the above diluted blood sample on top of the Ficoll-Paque. For each sample, two 15 ml tubes are used.
4. Centrifuge at 900 g, for 30 min at 18° C.
5. Carefully transfer the PBMCs from the interface into 50 ml tubes. Combine the cells from the two 15 ml tubes for the same sample.
6. Add PBS up to 50 ml and centrifuge at 900 g for 10 min.
7. Resuspend the cell pellet in 1 ml PBS and transfer into 15 ml tube.
8. Pass the sample through filter at 0.1-0.2 psi.
9. Take out the filter and put into a 1.5 ml Eppendorf tube. Add 50 µl CHAPS lysis buffer (Millipore, Temecula, Calif.) on top of the filter and keep on ice for at least 30 min.
10. Remove the filter and centrifuge at 14,000 rpm for 20 min at 4° C.

Run qPCR telomerase activity assay as described below.

Scanning Electron Microscopy (SEM)

The microfilter containing captured cells was fixed, rinsed, and mounted per standard protocol, then photographed on a scanning electron microscope with 3,500× magnification (JEOL JSM/6390LV).

Example 3

Quantitative PCR (QPCR) Telomerase Activity Assay

Telomeric Repeat Amplification Protocol (TRAP) Assay

Telomerase activity from cell extracts was analyzed using a previously described real-time PCR-based telomeric repeat amplification protocol (TRAP) (Xu T, Xu Y, Liao C P, Lau R, Goldkorn A. Reprogramming murine telomerase rapidly inhibits the growth of mouse cancer cells in vitro and in vivo. Mol Cancer Ther 2010; 9:438-49). The microfilter with captured cells was lysed in TRAPeze® 1×CHAPS Lysis Buffer (Millipore, 5 Temecula, Calif.), and 5 µl of cell lysate per reaction was added for each sample. For each reaction, DU145 cell lysates were used as standard controls in parallel.

QPCR telomerase activity assay was carried out as described below.

1. TS oligonuleotides (5' AATCCGTCGAGCAGAGTT (SEQ ID NO:1), 8 ng/µl) and 50 µM of each dNTPs are added to the cell lysate and incubated on a Bio-Rad MyiQ Thermocycler system for 30 min at 30° C. followed by inactivation of telomerase at 95° C. for 1 min.

2. ACX reverse primer (5'GCGCGGCTTACCCTTACCCT-TACCCTAACC (SEQ ID NO:3), SYBR green (1:20,000) and 0.8 U Taq platinum polymerase (Invitrogen, Carlsbad, Calif.) are added to the same tube in a master mix formula. The reaction is run on the same machine for 40 cycles at 95° C., 0"; 50° C., 5"; 72° C., 10", and the iQ5 optical system software version 2.0 was used to analyze the results.

Example 4

Figure 9A:
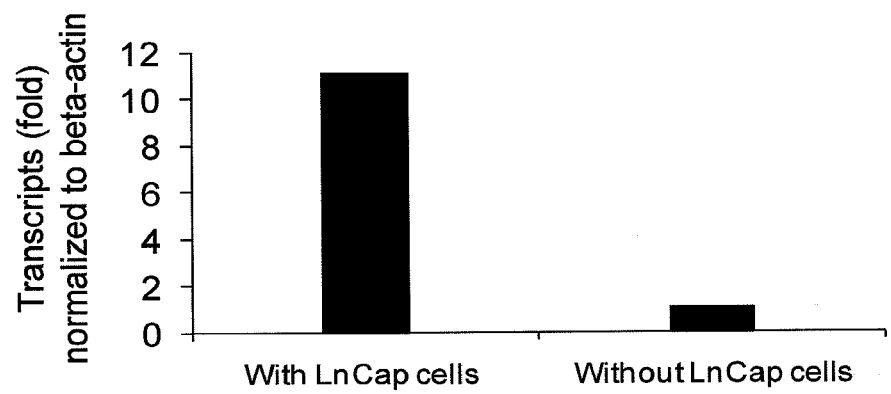
FIGS. 9A to 9B illustrate PCR for measuring transcript levels for genes of interest from cells live-captured on slot filter. Both quantitative/real-time PCR (A) and standard PCR (B) were performed for PSA transcript detection and measurement.
Figure 9B:
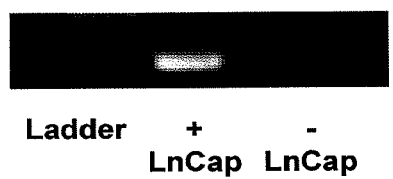

FIG. 9 shows measurement of PSA transcript levels from filter-captured cells. 100 LnCap cells were seeded into 1 ml fresh blood from healthy donor and passed through the parylene microfilter. RNA was isolated from microfilter-captured cells and cDNA was synthesized using commercially available kits. Both quantitative/real-time PCR (A) and standard PCR (B) were performed for PSA transcript detection and measurement. Compared to control blood without seeded LnCap cells, blood with seeded LnCap cells had least 12 fold PSA expression. These results constitute proof-of-principle for cancer cell capture by parylene microfilter followed by RT-PCR for detection and measurement of gene transcripts of interest.

What is claimed is:

1. A method for detecting and quantifying the telomerase activity of a viable circulating tumor cell, said method comprising:
    isolating the viable circulating tumor cell (CTC) from a sample using a parylene microfilter device comprising a membrane filter consisting of a parylene substrate having an array of holes, wherein the holes on the membrane filter have a rectangular shape each with a dimension of 5.5 µm to 6 µm by about 40 µm; and
    determining the telomerase activity of the isolated circulating tumor cell using a quantitative PCR telomerase activity assay.

2. The method of claim 1, wherein the step of determining comprises:
    obtaining a telomerase extension product; and
    amplifying the extension product by a quantitative PCR-based telomerase repeat amplification protocol assay.

3. The method of claim 2, wherein the step of obtaining comprises:
    (i) lysing the isolated circulating tumor cell to produce a cell lysate; and
    (ii) mixing the cell lysate with an oligonucleotide that is a substrate for telomerase extension to obtain an extension product.

4. The method of claim 1, wherein the sample is a peripheral blood sample.

5. The method of claim 1, wherein a quantitative PCR is used in determining the telomerase activity of the isolated circulating tumor cell.

6. The method of claim 1, wherein the step of isolating comprises passing the sample through the parylene microfilter device under a constant pressure.

7. The method of claim 6, wherein the pressure is between 0.1 to 0.3 psi.

8. The method of claim 1, wherein the array of holes is between 1 and 40,000 per square millimeter.

9. The method of claim 8, wherein the array of holes is at least 5,000 per square millimeter.

10. The method of claim 1, wherein the array of holes is between 1 and 850 per square millimeter.

11. The method of claim 1, wherein the holes have a dimension of 5.5×40 µm.

12. The method of claim 1, wherein the membrane filter has a figure of merit up to 890%/hr.

13. The method of claim 1, wherein the thickness of the membrane is at least about 1 µm.

14. A method for measuring telomerase activity in a single viable circulating tumor cell (CTC), said method comprising:
    isolating a group of CTCs from a sample using a parylene microfilter device comprising a membrane filter consisting of a parylene substrate having an array of holes with a predetermined shape and size, wherein the holes on the membrane filter have a rectangular shape each with a dimension of 5.5 µm to 6 µm by about 40 µm;
    obtaining individual viable CTCs from the group of CTCs isolated from the sample; and
    determining telomerase activity of said CTC.

15. The method of claim 14, wherein the step of obtaining comprises: using a micropipette to recover individual CTCs from the group of CTCs isolated from the sample.

* * * * *

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: synthetic telomerase (TS) extension
      oligonucleotide substrate, quantitative PCR (QPCR) amplification
      TS forward primer oligonucleotide

<400> SEQUENCE: 1
aatccgtcga gcagagtt                                                    18

<210> SEQ ID NO 2
<211> LENGTH: 16
<212> TYPE: DNA
<213> ORGANISM: Artificial Sequence
<220> FEATURE:
<223> OTHER INFORMATION: synthetic wild-type TTAGGG repeats

<400> SEQUENCE: 2
agggttaggg ttaggg                                                      16

<210> SEQ ID NO 3
<211> LENGTH: 30
<212> TYPE: DNA
<213> ORGANISM: Artificial Sequence
<220> FEATURE:
<223> OTHER INFORMATION: synthetic quantitative PCR (QPCR) ACX reverse
      primer oligonucleotide

<400> SEQUENCE: 3
gcgcggctta cccttaccct taccctaacc                                       30
```